(12) United States Patent
Meadows

(10) Patent No.: US 6,758,813 B2
(45) Date of Patent: Jul. 6, 2004

(54) METHOD TO UNIVERSALLY CONNECT APPLICATIONS DATA STREAMS TO VRML CONTENT

(76) Inventor: Jonathan L. Meadows, 3002 SE. Wisconsin, Topeka, KS (US) 66605

( * ) Notice: Subject to any disclaimer, the term of this patent is extended or adjusted under 35 U.S.C. 154(b) by 0 days.

(21) Appl. No.: 10/202,929

(22) Filed: Jul. 25, 2002

(65) Prior Publication Data

US 2004/0019257 A1 Jan. 29, 2004

(51) Int. Cl.[7] .................................................. A61B 5/00
(52) U.S. Cl. ...................................................... 600/300
(58) Field of Search ................................ 600/300–301, 600/544–545, 595; 128/904, 920, 905; 345/473, 418–419

(56) References Cited

U.S. PATENT DOCUMENTS

| 5,736,986 | A | 4/1998 | Sever, Jr. |
|---|---|---|---|
| 6,052,123 | A | 4/2000 | Lection et al. |
| 6,057,846 | A | 5/2000 | Sever, Jr. |
| 6,254,536 | B1 | 7/2001 | Devito |
| 6,348,927 | B1 * | 2/2002 | Lipkin ........................ 345/619 |
| 6,452,598 | B1 * | 9/2002 | Rafey et al. ................ 345/473 |

* cited by examiner

*Primary Examiner*—Max F. Hindenburg
(74) *Attorney, Agent, or Firm*—Bruce J. Clark

(57) ABSTRACT

A method for universally connecting proprietary or non-proprietary biofeedback data streams to multimedia content in a VRML environment, having the steps of acquiring the data streams with a predefined threshold value converting the data streams to values between approximately 0 and approximately 1 (where those values above approximately 0.5 represent success and those below 0.5 represent failure), and hooking the values to an eventIn of a node having a corresponding eventOut associated with it, and passing those values in a form suitable for interpolation.

6 Claims, 5 Drawing Sheets

Independently Definable Success and Failure Range

IADV Scale

ADV Scale

METHOD TO UNIVERSALLY CONNECT APPLICATIONS DATA STREAMS TO VRML CONTENT

BACKGROUND OF THE INVENTION

This invention relates to the fields of biofeedback and virtual reality programming.

In the certain fields of virtual reality programming, it is often desirable to convert one or more streams of data so as to be displayed on screen in an effective manner, reflecting as meaningfully as possible the three-dimensional (3D) scene intended for display. Doing so typically requires a significant amount of programming customized code for the expected stream of data that will be interpolated and used to create a 3D scenegraph. When multiple streams of data are utilized the executable code is that much more intertwined with the particular 3D scenegraph and thus even more complex to modify. Changes in the scenegraph or "content", whether small modification or entire replacement, require extensive and tedious programming endeavors at source code programming levels. There exists a need for a method to allow an entire 3D scenegraph to be both modifiable and responsive to input data streams, without significant rewriting of the executable code.

In the biofeedback field, for example, patients view a screen that displays a 3D "game" (content) responsive to the multiple input data streams from sensors detecting the user's physiological data. Modifying these "games", or creating new ones, typically involves modifying source code and recompiling a new executable.

For a computer to display a 3D scene, a moving spaceship, for example, that is responsive to input data (i.e. the spaceship moves in response to and dependent on values from a stream of data), the data must be interpolated (called an Interpolation in VRML specifications), i.e. points for use on the display must be calculated between two chronologically defined data points, so as to enable, for example, the spaceships to appear to move smoothly. This spaceship is created and shown in the desired moving fashion by a program utilizing a 3D rendering engine. A typical rendering engine that displays and interpolates in the preferred embodiment is that sold by Parallel Graphics.

Although rendering engines are standard in 3D graphics applications, using them to create a new "game" in a biofeedback or other setting requires a significant amount of programming by the "games" developer (here the "content developer).

In the biofeedback field, the proprietary computer systems utilize proprietary software, and sometimes proprietary hardware, to develop these "games" or "content" that the patient "plays" within the biofeedback exercises. For example, the patient may try to keep a car on a highway, on screen, by controlling his/her mental state or blood pressure, or it might be a space ship that moves in response to the desired, or undesired, actions of the patient as measured by the sensors detecting the targeted bodily or mental functions. These games also typically require significant programming that make the task of modifying them or developing new ones time-consuming.

The need for uniformity and ease of programming is complicated somewhat in the biofeedback arena. PC-based biofeedback systems are designed in various ways. Some systems focus solely on EEG biofeedback (neurofeedback). Some systems focus solely on peripheral (everything but brainwaves) biofeedback. Some systems facilitate clinician design of feedback protocols combining peripheral and EEG measurements (at the expense of complexity) Other systems are tuned to provide only a very specific kind of training (at the expense of total capabilities). Still other systems focus on multi-site EEG data acquisition. No single system is known that is capable of acquiring every kind of physiological measurement used for biofeedback training, and there is no known single system capable of every type of training protocol. Biofeedback clinicians purchase systems that best address the needs of their clinic and the kind of training services they provide.

Currently available biofeedback systems have focused on the best ways to gather and process the physiological data, and the ways to best present that information to the clinician. However, the current systems have not focused much on ways to intuitively convey this information to the person receiving the biofeedback training. Given the widening acceptance of biofeedback as a viable treatment for numerous conditions, the development of more varieties of biofeedback protocols, and the potential growth in complexity of the real-time data presented to the biofeedback client, more intuitive methods of conveying feedback information to the client (i.e. new "content") are desired and will be needed.

Whether it be biofeedback games, mainstream entertainment games, or other "content" that uses multiple data streams for input, the developer must make tedious, substantial, and sometimes fundamental changes to the executable code for meaningful changes in the behavior or control of the visual and auditory "content". A method is needed, so as to reduce the task of creating content significantly.

The inventive process advances all of these interests to allow a much more flexible and universal method to connect proprietary biofeedback software or other software providing multiple data streams, to VRML-based software for providing feedback to the user, so as to make it possible for VRML content to be created for any system, biofeedback or otherwise, in an efficient, system independent, and reusable way without significantly (if any) recoding of an executable.

VRML (pronounced Ver-Mul) is an acronym for Virtual Reality Modeling Language. It is a standardized language for describing three dimensional modeling and animation of geometric objects. VRML allows a 3D scene to be manipulated in real-time and provides for the organization of objects within scenes in a hierarchical fashion. A VRML scene may include any number of objects. A VRML scene may also contain animations (object behavior). Using VRML, a 3D scene is defined in a written language in terms of nodes, fields, and events. Nodes are abstractions of real-world objects and concepts. Examples of nodes include shapes, lights, textures, sounds, sensors, timers, scripts, and interpolators. Nodes contain fields and events. A field is a property or attribute of a node that can hold and sometimes receive and/or pass a value. Fields may contain data and one or more values, much like a variable or array does in computer programming. There are two types of events—eventIn and eventOut. Messages can be sent between nodes along routes that are connected via an eventOut to an eventIn. A field that's combined with an eventIn and eventOut has the characteristics of all three components and is called an exposedField. Each type of node has a fixed set of fields. Nodes are organized into a hierarchical representation of a 3D scene called a scenegraph. VRML is the only ISO (International Standards organization) ratified standard for 3D over the internet.

It is therefore an object of the invention to create a process for easily and universally interfacing biofeedback and other applications to virtual reality, to allow for relatively quick and easy creation and implementations of new or modified content, responsive to the anticipated streams of data, and with a minimum of executable level (or lower level) programming.

The inventive process creates a proprietary program andd proprietary VRML node to comprise an interface between the content developer utilizing VRML and the proprietary biofeedback or other acquisition system that exports data streams so as to allow for a universal connection to the proprietary system, allowing content developers the freedom, to easily and quickly develop new content.

Other objects and features of the invention will be apparent as set forth in the detailed description and claims.

DESCRIPTION OF THE PREFERRED EMBODIMENTS

Figure 1:
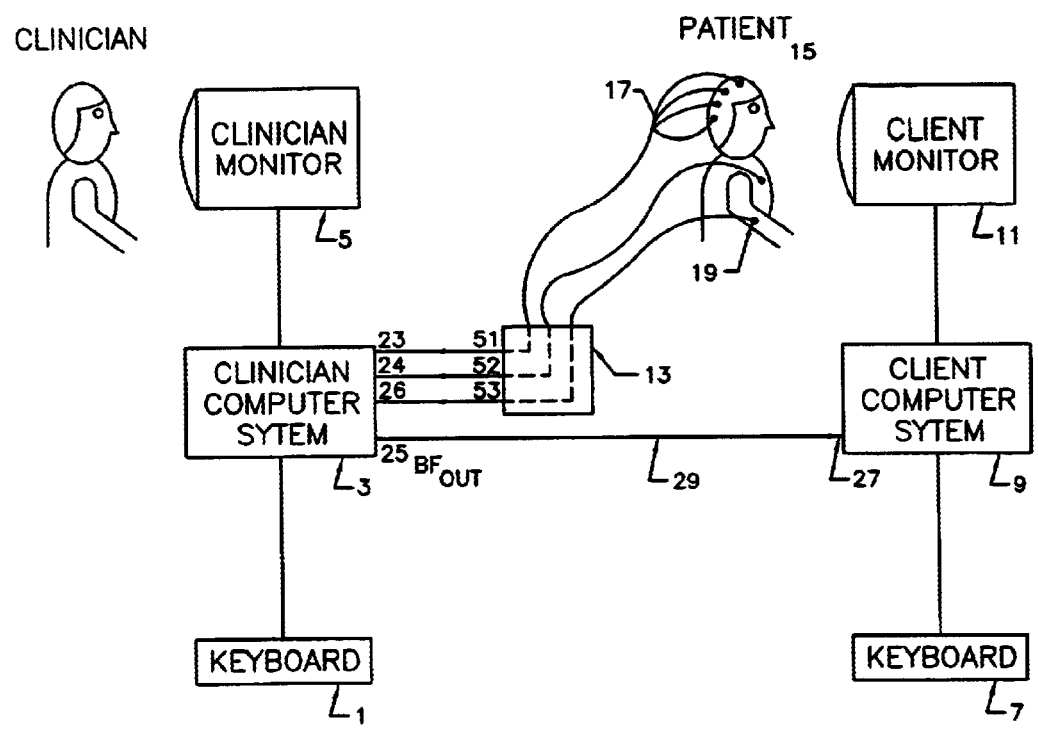
FIG. 1 is a general layout of the equipment and setup in a biofeedback setting.

The typical system setup and arrangement for practicing the invention in the biofeedback application is shown in FIG. 1. Two computer systems 3 and 9, with keyboards 1 and 7 are shown although these can also be combined into one system. In either arrangement, separate monitors 5 and 11 are recommended in the preferred mode for viewing by the clinician and client independently.

The client computer is shown with its own keyboard 7 and client monitor 11 for operating and viewing by the client, who in some instances may be considered a patient. This system in the preferred mode and under existing technology is a minimum PENTIUM and WINDOWS 95 or later version (depending upon the VR content intended to be displayed) with hard-drive storage means, although other storage means are envisioned. The client monitor is a standardly available monitor preferably having at least a 120 Hz refresh rate for stereoscopic display (e.g. using shutter glasses). A graphics card with functions for hardware acceleration is recommended.

The invention can be practiced with other systems including gaming systems and control systems and is compatible with any other CPU-based systems such as Motorola manufactured CPU's and with other operating systems including but not limited to Unix, Linux, or proprietary systems.

The clinician computer 3, with standard keyboard 1, has in the preferred mode under existing technology the same preferred requirements as the client computer, although it can even be a DOS-based system as is still sometimes encountered in the art. The clinician computer 3 is typically provided by a third party also providing the acquisition hardware (amplifier 13) and acquisition software, which software resides on the clinician computer 3, the amplifier 13, or both.

Further required is a program utilizing 3D brendering engine, capable of displaying data files compliant with the VRML 2.0 specification. An example of a rendering used in the preferred mode is Cortona by Parallel Graphics.

The inventive process is in the preferred mode, within the interface program referred to as the CIS, Cybernetic Interface System, which in the preferred mode resides on the client computer 9.

The amplifier 13 is typically a proprietary hardware device and is sometimes referred to as the acquisition hardware because of its role in first acquiring the physiological signals from client (patient) 15 usually via sensor cables. These sensors in a typical biofeedback arrangement are connected to parts of the body as deemed necessary by the clinician and usually include contact points on the head 17 and arms 19 to measure different physiological variables derived from electrical currents, impedance, blood flow and temperature, for example, or anything measurable. In the typical mode, these are converted to electrical signals and amplified by the acquisition hardware (amplifier) 13.

Some proprietary acquisition systems also provide for the amplifier to further convert the analog signals to digital data to provide for better integrity of the signal in certain situations. The amplifier is connected to the clinician computer 3 typically via serial, USB, or ethernet cable, although any of numerous connections are possible. It is envisioned that the amplifier and clinician computer can be integrated into a single proprietary black box of hardware and software that acquires the signals from the sensors and converts them to the digital data to be used by the client computer 13 at the biofeedback out, BF/out (25).

Typical proprietary client computer/acquisition systems include those manufactured by NeuroCybernetics, Thought Technology (Biograph), and Brainmaster Technologies (Brainmaster). It should be understood that any communication method envisioned includes communication by hardwire, wireless, or any other communication method.

These proprietary systems, as indicated, export data at BF/out 25, referred to as data streams and commands, which are acquired by the client computer at 27 via any typical computer input port as desired (USB, serial, parallel, ethernet, and MIDI).

The data streams are in digital format are comprised of a range of values representing the information sensed and acquired by the sensor(s) and amplifier, which range is determined by the proprietary acquisition system in use. This range of data values is typically between 0 and 128 although other ranges have been used or are envisioned, such as 0 to 60, 0 to 256, −1 to +1, or even −65536 to 65536.

Commands can be exclusive to the proprietary acquisition system or they can be commands that are proprietary to the CIS software in situations where a portion of the CIS software resides on the clinician computer. Commands include, for example, when to award a point for certain behavior, or when to initiate some action such as changing color, or to titrate the reinforcement schedule. This tells the CIS to do the steps necessary to cause the screen to do the desired things necessary so as to reinforce the client behavior.

While commands are important to the invention, the data streams are of primary importance. In a system where the data stream is in a digital format representing 0 to 128 as the range of values for any signal, the acquisition system not only converts the signal from each sensor 23, 24, 26 to corresponding individual data streams at BF/out having a value between 0 and 128, but the acquisition system also, according to its proprietary design needs, computes other derivative signals, called here Computed Data Streams, based on signals at 23, 24 and 26 and converts them each to a value between 0 and 128 and exports them at BF/out. For example, the output at BF/out might not only have three data streams representing signals at S1, S2, S3, but might also have Computed Data Streams representing the amplitude, the difference between signals, the rate of change, frequency, etc. All data streams in this detailed description herein have a value between 0 and 128.

These Computed Data Streams are usually modifiable by the clinician operating the acquisition system (clinician computer 3). Consequently, if it is important to a clinician to measure and/or observe the amplitude of S3 in relation to the amplitude of S2, he can instruct the acquisition system to compute and export such a data-stream, again having a value between 0 and 128 in this example. Other computed data streams could each simply be derived from one sensor alone such as acquiring the different amplitudes of different frequency ranges that might be sensed by any individual sensor. There are anywhere from one to several thousand possible data streams, but more commonly there are two to six in number.

The client computer 9 typically has installed on it the CIS program. This is the executable that in the preferred mode, practices the basic concept of the invention. This CIS program acquires at 27 each data stream being exported by the acquisition system at BF/out. The cable 29 in this embodiment is a serial data cable connected between the two computers 3 and 9 via their respective RS232 ports, although any method of communication between the computers is envisioned, including parallel, wireless, ethernet, MIDI, Internet or other.

Figure 2:
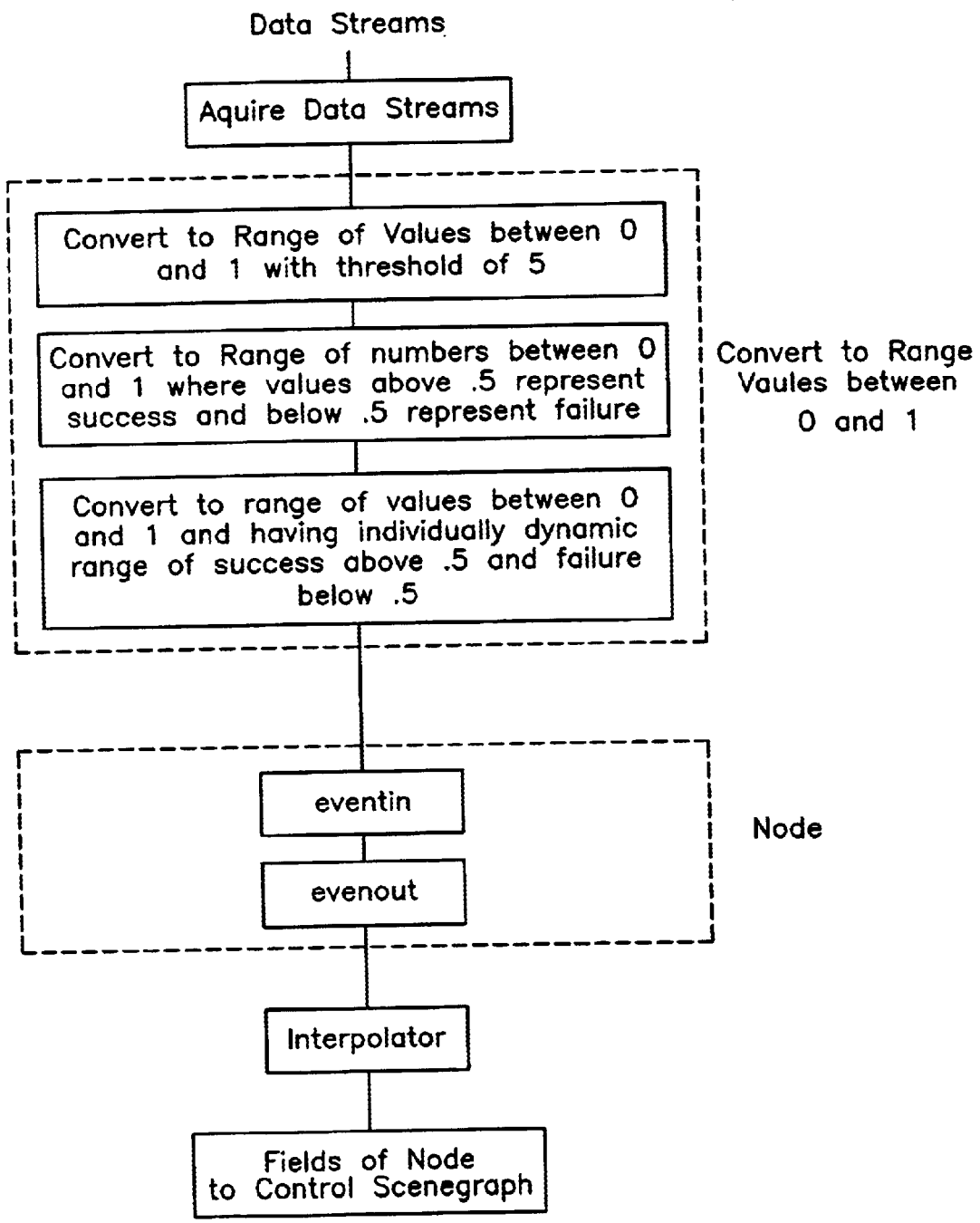
FIG. 2 is a Flow Chart showing the inventive steps.

More specifically, the inventive process is described and carried out as follows:

The inventive process in the preferred mode is described in FIG. 2. Data streams that are generated by the clinician computer 3 are acquired by the CIS in client computer 9. These data streams are converted to a predefined range of values, preferably between 0 (approximately) and 1 (approximately). If a threshold is defined (as is typically the case in the proprietary biofeedback acquisition system), such that the threshold as a data value above or below which events are to be positively or negatively reinforced by causing a desired effect to occur in the scenegraph, then a conversion process takes place to convert the data stream values above or below threshold such that the converted data values representing behavior to be positively reinforced is greater than (approximately) 0.5 in the converted data streams. Data values representing behaviors to be negatively reinforced are converted to values less than (approximately) 0.5 in the converted data stream in the preferred mode. A dynamic range is set on each side of threshold, each independently defined, that determine a success or failure. The converted data streams are then hooked to fields (eventin) of a node, which fields also correspond to eventouts. The converted data stream is then routed, or made available to be routed, to desired fields of a mode in the scenegraph for further processing as a content developer desires in creation of the particular desired content.

Regardless of the type(s) of proprietary input data streams, the content developer using this process will need only know the VRML specifications for access to each data stream or other data, including commands, passed along and/or converted by the CIS, allowing the content developer to work only in the VRML environment to create or modify content.

In an alternative mode, the process provides for an "on the fly" modification, that even allows the clinician himself to revise certain content in a limited manner. This is done by providing first a plurality of primary-command options available to the clinician through an on-screen frame or window, routing each primary-command to a set of commands within a script node, where each command independently effects behavior within the scenegraph.

As a further explanation, the CIS first acquires the data streams, recognizing each separate data stream in a manner consistent with the communication protocol defined by the proprietary acquisition system sending the data. For example, in an acquisition system using MIDI communications protocol, data is sent through that respective port (MIDI-out of acquisition system) to the MIDI-in of the client system and subroutines utilizing the MIDI protocol to identify each of the data streams. In such a system, each MIDI note or MIDI channel separately contains each data stream and the MIDI system-Exclusive message contains any command. In the current example, utilizing serial ports, other methods are envisioned to send data streams, including the byte pair method. In the byte-pair method the first byte of a byte-pair identifies what the next byte represents (e.g. which data streams, a command, a new threshold value, whether to award a point, or whether to "go to the next screen"). The second byte represents the value. The data communication protocol is usually proprietary to the acquisition system. The values are usually affected by the clinician. For example the clinician can set or change a threshold on the fly.

The CIS executable is programmed first to identify each data stream, command, and value in a fashion corresponding to the communication protocol utilized by the acquisition system.

For each data stream coming out of the acquisition system at BF/out and for each value identified, the CIS executable then converts it to the CIS format. This is done by assigning a value of between 0 and 1 to the value received from each incoming data stream. In the preferred mode, two values are established, referred to herein as either an Absolute Dynamic Value (ADV) or Relative Dynamic Value (RDV) as desired, and defined further herein.

It should be understood here that the data streams are comprised of values proprietary to the acquisition system and include usually the data value, as well as an indication as to whether the data represents a Success or a Failure, i.e. whether the data is to be treated as something needing to be positively or negatively reinforced in the biofeedback process. In many systems this is a threshold indication or threshold value. Most systems currently have a threshold value, whereby a data value above or below the threshold value is considered a success or failure. For example in a system where the data ranges are between 0 and 128, a threshold value of 32 means that a value above (or below) 32 is considered a success (or failure) so as to cause the scene on the monitor 11 to change in a way to positively (or negatively) reinforce the viewing client's behavior. For example, if the clinician wants to augment certain brain activity being measured and transmitted in a data stream, higher values (above threshold) might be considered a success (and thus be positively reinforced), and values below threshold would then be considered a failure. This would be considered an Enhance data stream in such a system. An Inhibit data stream in such a system is one where the values below threshold are considered success, i.e. the conduct to be positively reinforced generates values preferably below threshold, and the more the client "inhibits" the conduct (such as creating lower values for lower blood pressure or suppressing brainwaves associated with lack of focus) the further the values get below threshold.

It should be understood that some acquisition systems communication protocol are such that the data coming from them is already known to be an Enhance or Inhibit type. In some systems, the very nature of the data indicates whether it is Enhance, or Inhibit, such as in a MIDI system that communicates certain musical notes for Enhance and other notes for Inhibit. There are still other methods used to differentiate between the success and failure data. It is only significant that by using the acquisition system's proprietary communication protocol(s), the CIS can identify for each incoming data value whether the data is to be positively or negatively reinforced.

In the system shown herein where the data values are between 0 and 128 and where there exists a threshold above or below which the value is to be positively or negatively reinforced (Enhanced or Inhibited), it is necessary to convert these two different types of data streams (Enhance and Inhibit) to the CIS format. In this format, these two types of data streams (Enhance that has success values above threshold and Inhibit that has success values below threshold), must be converted to a value between 0 and 1 where 0.5 or above represents success in either case (for either Enhance or Inhibit) and values below 0.5 represent failure. To do this the threshold value must be known as well as whether the data stream is an Enhance or Inhibit type. This conversion process performed by the CIS executable will convert both the Enhance and Inhibit data streams to an Absolute Dynamic Value (ADV) (mapped linearly to the amplitude of the value without reference to time or rate of change) and then a Relative Dynamic Value (RDV) (rate and degree of change).

Figure 3:
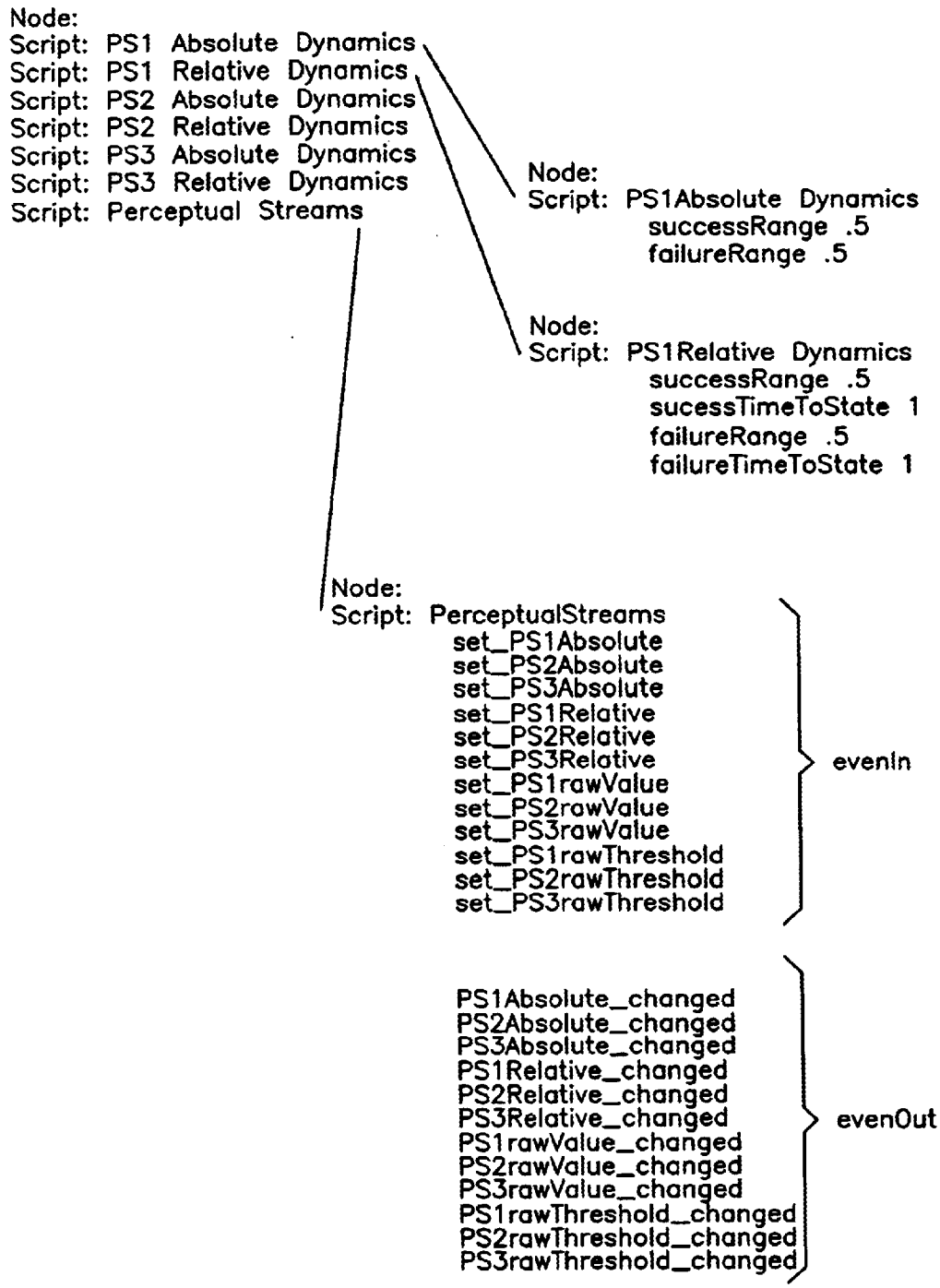
FIG. 3 shows the Node showing the various data streams.
Figure 4:
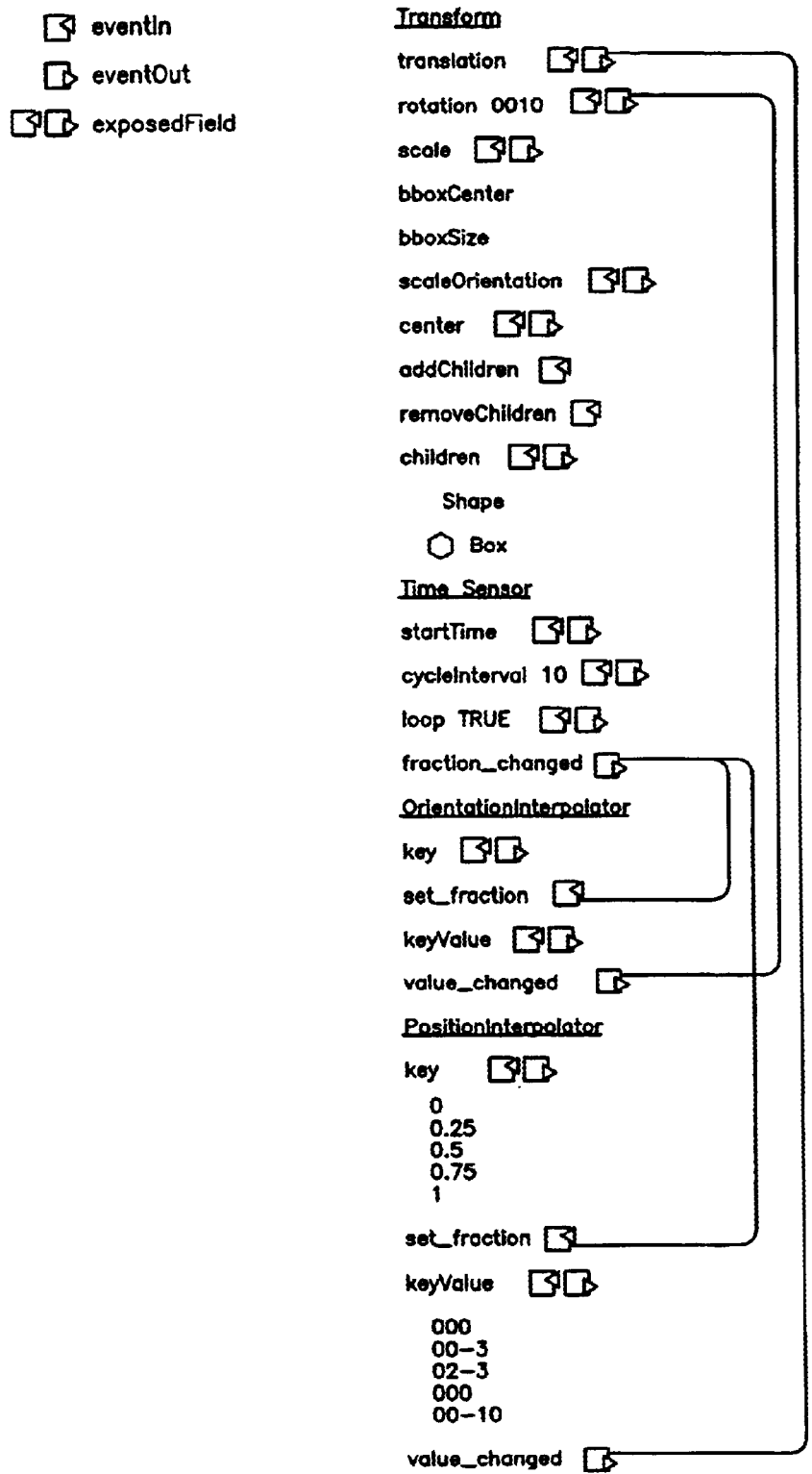
FIG. 4 shows the Fields in an Interpolator using some sample data.

One or both of these converted data streams, as desired, are hooked to a field of a node in the scenegraph. In FIG. 3 these are shown hooked to the eventIns of a noded named "PerceptualStreams" as, for example, "Set_PS1Absolute" and "SetPS2Absolute", etc., which eventIn fields correspond to eventOut fields "PS1Absolute_Changed", "PS2Absolute_changed", etc. The values going out the eventOuts are now available to eventIns of Interpolator nodes for example FIG. 4, for effecting changes in the scenegraph. As is seen in FIG. 4, each node within the scenegraph represents desired characteristics of the display, such that each field controlled by incoming data streams is responsive to the respective range of numbers utilized to create the converted data streams and such that the scenegraph and display to the client will reflect success and failure data responsive to the threshold values. This allows the content developer a consistent, predictable and unified means to control interpolators used to cause an action in the scene to occur.

Figure 5:
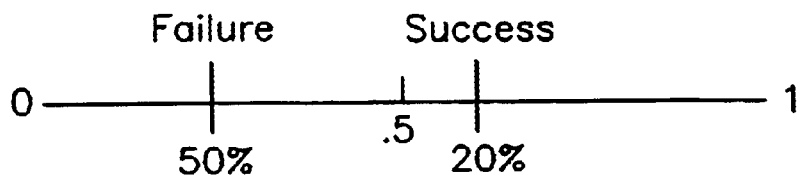
FIG. 5 illustrates the independently definable Success and Failure range.

It will be seen in FIG. 3 that the dynamics for the success range and failure range, related to the threshold, are modifiable independently, via the node named "PS1AbsoluteDynamics" for example. This success range and failure range are discussed further herein, but it can be seen in FIG. 5 that as part of the conversion process, a failure range can be set at 50%, for example, and a success range independently set at 20% for example, giving the content developer further flexibility in design of content.

To convert the incoming data streams to the ADV. (Absolute Dynamics Value) in the current example wherein the data values are between 0 and 128, and where the Enhance and Inhibit types are distinguishable from each other, one must know the threshold values and convert independently in a different manner the Enhance and Inhibit values. The objective is to convert the data values to a relative value between 0 and 1 where 0.5 or above 0.5 is a success and below 0.5 represents failure.

To do this, in the preferred mode, an Intermediate Absolute Dynamics Value (IADV) is determined and this IADV is then used to determine the ADV.

One must first define the Success Range and Failure Range that determine a corresponding Ceiling (and Floor) above (or below) which is considered maximum success (or failure) as appropriate. The Success Range, for example, might be set at between threshold and 60 percent above threshold, which means that any values in the data stream greater than 60 percent above threshold hit the Ceiling and are considered a success and given the same converted value of 1. This allows for the situation where some content needs to have different dynamic characteristics for positive reinforcement than its dynamic characteristics for negative reinforcement. For purposes of the Floor, any values less than a certain percentage below threshold would be considered failure in this example and given the same converted value of 0.

Figure 6:
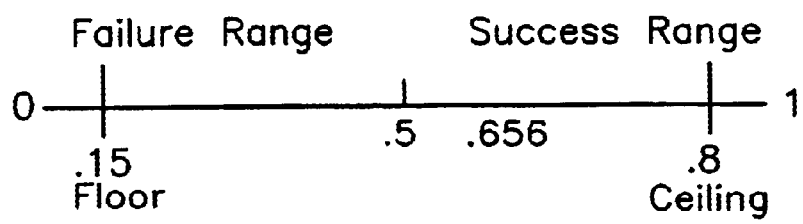
FIG. 6 shows the Intermediate Absolute Data Value (IADV) and the relationships, as well as the ceiling and the floor in the example discussed.

The Success Range and Failure Range are defined in fields of nodes, e.g. PS1 . . . Dynamics in FIG. 3. They are default settings that are typically set by the content developer, although the content developer sometimes provides for the ability of the clinician to titrate these values. In this example, a Success Range of 60 percent will therefore provide a Ceiling of 0.8 ((0.6×0.5)+0.5) on the Intermediate Absolute Dynamic Value (IADV) scale in FIG. 6. The Failure Range, which in this example will be set at 70 percent (70 percent below threshold) produces a Floor of 0.15 (0.5−(0.7×0.5)). The Ceiling, the Floor and the Intermediate Absolute Data Value of 0.656 (Enhance, but 0.381 if using Inhibit) are placed on the IADV scale in FIG. 6 for illustrative purposes. Thus we have determined where the Intermediate Absolute Data Value (IADV) is with respect to the Success and/or Failure Range respectively. (FIG. 6)

Figure 7:
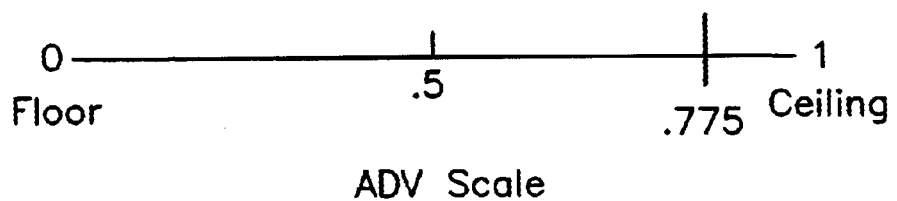
FIG. 7 shows the Absolute Data Value (ADV) and the relationships, with reset Ceiling and Floor, in the example discussed.

At this point the IADV has been determined as a number between zero and one, where values above the Ceiling and below the Floor have been deemed essentially irrelevant to the extent they are above the Ceiling and Floor. Consequently, the next step is to convert the IADV to a more usable ADV that consists of a number between zero and one where zero and one correspond to the Floor and Ceiling of the Failure Range and Success Range respectively. To do this the IADV is converted to an ADV which ADV is proportionately between the threshold of 0.5 and the Floor or Ceiling the same percentage, for success as the IADV was above threshold with respect to the IADV Ceiling of 0.8). To do this subtract the Threshold (0.5) from the Ceiling (0.8) to arrive at a denominator (0.3), then use as a numerator the IADV (0.665) minus the Threshold (0.5), then divide the number to arrive at a percentage above Threshold that the IADV exists in relation to the Ceiling of the Success Range in FIG. 4. In this case, 0.165/0.3=0.55, or 55 percent above threshold. Consequently on the new scale 0.5 remains the threshold, and the ADV is 55 percent above 0.5, therefore the Absolute Dynamic Value is 0.775 shown in FIG. 7.

A Relative,Data Value RDV) is then created if required or desirable that is dynamic and changes with each new incoming data value, which essentially is the rate of change of the movement of the data points along the scale, i.e. it is a time based set of values. This will cause the action in the monitor to be relative to the success or failure, which allows for the desired object (shape, size, color, etc.), to change faster, the greater the success or failure of the response, as desired. This allows more flexibility for the content developers and the particular needs of a scene to control the behavior of object therein. To determine the RDV, in the preferred mode, an intermediate IRDV is first created from the ADV, then that IRDV is rescaled to calculate the RDV.

The data stream has now been converted to two new data streams, one having Absolute Dynamic Values mapped linearly to the incoming data values, the other having Relative Dynamic Values (related to the speed at which the data point in the 0 to 1 scale moves toward the ceiling or floor). While the preferred mode calculates them with either or both being ultimately utilized.

The Absolute Dynamic Value and the Relative Dynamic Value (if both are required for the content developer's purpose) are then inputed to eventIns of nodes in the scenegraph (FIG. 3), which have corresponding eventOuts. This arrangement provides the means in which the converted value of incoming data streams can be routed to interpolators used by the content creator to control animations within the scene.

For example, it will be seen in FIG. 3 that script node 3 has various eventIns for both the absolute and relative types. It should be noted that a third type of eventIn is available for receiving incoming data stream values. These "raw value" eventIns are comprised of the nonconverted data at BF/out. It will be seen in FIG. 3 that there are three of each type in the example (PS1, PS2, and PS3) although any number may be present, as desired. Also shown is the raw-threshold value for each PS1, PS2 and PS3. All of these eventIns (absolute, relative, raw and raw-threshold) receive values sent by the CIS executable.

In use, the CIS program (which typically encompasses the inventive steps) resides on the client computer. The CIS acquires from the acquisition system the raw data streams. The CIS converts the data stream(s) to a desired number between 0 and 1, where those equal to 0.5 or above represent success, and below 0.5, failure, for each desired data stream in a manner desired by the CIS programmer to achieve the ultimate responsiveness desired in the scenegraph, then passes the values of the converted data stream(s) to the fields in the desired nodes for direct access by the content developer. This gives the VRML content creator the means to change content easily and quickly without modifications to the CIS executable being necessary. Content creators only need know the basic node declaration and routing specification utilized by the CIS programmer.

Consequently it can be seen that a unique and useful method is disclosed for universally connecting proprietary or non-proprietary data acquisition systems, including biofeedback systems, to VRML content so as to facilitate relatively rapid and easy modification and development of virtual reality content.

I claim:

1. A method to universally connect biofeedback applications software to VRML content for providing positive or negative reinforcement to client behavior, utilizing physiological sensing devices and a computer, comprised of the steps of:

a. creating a plurality of data streams of values desired to be represented and perceived in a VRML environment whereby each data stream represents the stream of data corresponding to at least one physiological measurement sensed;

b. converting the values in each data stream to a converted data stream having digitized values each value representing a desired range of numbers and having a threshold value between the minimum and maximum converted value in which data values above or below the threshold value indicate the need for positive or negative reinforcement of client behavior;

c. inputting the converted data streams to an eventIn of a node that is associated with a corresponding eventOut of a node, which eventOut makes the converted data stream available to a node for eventual interpolation;

d. inputting the converted data stream from eventOut to said node;

e. computing the interpolated values of the converted data stream to create an interpolated data stream of values;

f. inputting the interpolated data streams to fields representing desired characteristics of the display within the scenegraph and such that each field is responsive to the respective desired range of numbers utilized to create the converted data stream.

2. The method in claim 1 when the value between the minimum and maximum converted value in which a threshold value exists between the desired range of values such that the threshold is a data values above or below the threshold value indicate the need for positive or negative reinforcement of client behavior.

3. The method in claim 2 having a desired range of values and threshold such that the dynamics of the positive reinforcement can be set independently of the dynamics of the negative reinforcement on either side of threshold.

4. The method in claim 1 when inputting the interpolated data streams to fields representing desired characteristics of the display within the scenegraph and such that each field is responsive to the respective desired range of numbers utilized to create the converted data stream.

5. The method in claims 1, 2, or 3 where the desired range of numbers is essentially 0 to essentially 1.

6. The method in claims 1, 2, or 3 having the additional steps of selecting a desired clinician command from a plurality of predefined commands, where each command corresponds with a set of commands within a script node that affect the predefined desired options of behavior within the scenegraph, then sending said selected clinician command to the script node, providing for real time modification of the scenegraph by the clinician.

* * * * *